(12) United States Patent
Tian et al.

(10) Patent No.: US 12,420,110 B2
(45) Date of Patent: Sep. 23, 2025

(54) METHODS AND SYSTEMS FOR MODULATING CELLULAR ACTIVATION

(71) Applicant: The University of Chicago, Chicago, IL (US)

(72) Inventors: Bozhi Tian, Chicago, IL (US); Menahem Rotenberg, Chicago, IL (US); Aleksander Prominski, Chicago, IL (US)

(*) Notice: Subject to any disclaimer, the term of this patent is extended or adjusted under 35 U.S.C. 154(b) by 193 days.

(21) Appl. No.: 17/768,329

(22) PCT Filed: Oct. 16, 2020

(86) PCT No.: PCT/US2020/056106
§ 371 (c)(1),
(2) Date: Apr. 12, 2022

(87) PCT Pub. No.: WO2021/076981
PCT Pub. Date: Apr. 22, 2021

(65) Prior Publication Data
US 2024/0100354 A1    Mar. 28, 2024

Related U.S. Application Data

(60) Provisional application No. 62/915,928, filed on Oct. 16, 2019.

(51) Int. Cl.
*A61N 5/06* (2006.01)

(52) U.S. Cl.
CPC ...... *A61N 5/062* (2013.01); *A61N 2005/0626* (2013.01); *A61N 2005/0659* (2013.01); *A61N 2005/0662* (2013.01)

(58) Field of Classification Search
CPC ............ A61N 5/062; A61N 2005/0626; A61N 2005/0659; A61N 2005/0662; A61N 5/067; A61N 5/0603; A61N 2005/063; A61N 1/36; A61N 5/0622
See application file for complete search history.

(56) References Cited

U.S. PATENT DOCUMENTS

| | | | |
|---|---|---|---|
| 9,592,292 | B1 | 3/2017 | Beckman et al. |
| 10,663,450 | B2 | 5/2020 | Tian et al. |
| 2007/0282247 | A1 | 12/2007 | Desai |

(Continued)

FOREIGN PATENT DOCUMENTS

| | | | | |
|---|---|---|---|---|
| WO | 2019/168714 | A2 | 9/2019 | |
| WO | WO-2019168714 | A9 * | 10/2020 | ............ A61K 33/00 |

(Continued)

OTHER PUBLICATIONS

Jiang, Y., et al., "Rational Design of Silicon Structures for Optically Controlled Multiscale Biointerfaces", Nature Biomedical Engineering, Jul. 2018, vol. 2(7), pp. 508-521.

(Continued)

*Primary Examiner* — Rex R Holmes
(74) *Attorney, Agent, or Firm* — Alexa L. Dian

(57) ABSTRACT

This disclosure relates to methods for modulating activity of cells and tissue with materials that are capable of being activated by light, such methods useful for treating diseases. The disclosure also provides devices and systems suitable for use in such methods, particularly devices and systems having oxygen plasma-treated p-type (boron) silicon.

12 Claims, 13 Drawing Sheets

(56) References Cited

U.S. PATENT DOCUMENTS

| | | |
|---|---|---|
| 2009/0054954 A1 | 2/2009 | Foley et al. |
| 2009/0088680 A1 | 4/2009 | Aravanis et al. |
| 2011/0024309 A1* | 2/2011 | Lee ................. G01N 33/54373 205/792 |
| 2011/0125078 A1 | 5/2011 | Denison et al. |
| 2011/0270153 A1 | 11/2011 | Olson |
| 2012/0034622 A1 | 2/2012 | Ignatius |
| 2012/0136296 A1 | 5/2012 | Peyman |
| 2012/0301446 A1 | 11/2012 | Zhu |
| 2013/0274838 A1 | 10/2013 | Entcheva et al. |
| 2014/0236267 A1 | 8/2014 | Parker |
| 2017/0326381 A1 | 11/2017 | Kozai et al. |
| 2018/0311508 A1 | 11/2018 | Ellingwood |
| 2019/0030190 A1 | 1/2019 | Peyman et al. |
| 2020/0390803 A1 | 12/2020 | Tian et al. |
| 2021/0033559 A1 | 2/2021 | Panat |
| 2023/0048814 A1 | 2/2023 | Tian et al. |
| 2023/0183075 A1 | 6/2023 | Tian et al. |
| 2024/0009630 A1 | 1/2024 | Tian et al. |
| 2024/0100354 A1 | 3/2024 | Tian et al. |
| 2024/0101997 A1 | 3/2024 | Tian et al. |

FOREIGN PATENT DOCUMENTS

| | | |
|---|---|---|
| WO | 2021/076981 A1 | 4/2021 |
| WO | 2021/138089 A1 | 7/2021 |
| WO | 2021/242425 A2 | 12/2021 |
| WO | 2022/125328 A2 | 6/2022 |
| WO | 2024/076353 A2 | 4/2024 |

OTHER PUBLICATIONS

Thess, et al., "Crystalline Ropes of Metallic Carbon Nanotubes," Science, Jul. 26, 1996, vol. 273(5274), pp. 483-487.
International Search Report from the European Patent Office, mailing date of Feb. 5, 2021, for International Application No. PCT/US2020/056106, pp. 1-6.
Written Opinion from the International Searching Authority, mailing date of Feb. 5, 2021, for International Application No. PCT/US2020/056106, pp. 1-7.
Dalby, M.J., et al., "Harnessing Nanotopography and Integrin-Matrix Interactions to Influence Stem Cell Fate", Nature Materials, May 21, 2014, vol. 13, pp. 558-569.
Gentemann, L., et al., "Modulation of Cardiomyocyte Activity Using Pulsed Laser Irradiated Gold Nanoparticles", Biomedical Optics Express, Dec. 8, 2016, vol. 8(1), pp. 177-192.
Jiang, et al., "Rational Design of Silicon Structures for Optically Controlled Multiscale Biointerfaces", Nature Biomedical Engineering, Jul. 2018, vol. 2(7), pp. 508-521.
Kabat, et al., "Sequences of Proteins of Immunological Interest U.S. Department of Health and Human Services, Bethesda" Nakamaya, K. and Eckstein, F., Nuc. Acids Res., 1991, vol. 14, pp. 9679-9698 (Abstract only).
Parameswaran, R., et al., "Photoelectrochemical Modulation of Neuronal Activity with Free-Standing Coaxial Silicon Nanowires", Nat. Nanotechnol., Feb. 19, 2018, vol. 13(3), pp. 260-266.
Parameswaran, R., et al., "Optical Stimulation of Cardiac Cells with a Polymer-Supported Silicon Nanowire Matrix", PNAS, Dec. 11, 2018, vol. 116(2), pp. 413-421.
Thess, et al., "Crystalline Ropes of Metallic Carbon Nanotubes," Science, Jul. 26, 1996, vol. 273, Issue 5274, pp. 483-486.
Tian, B., et al., "Three-Dimensional, Flexible Nanoscale Field-Effect Transistors as Localized Bioprobes", Science, Aug. 13, 2010, vol. 329, pp. 830-834.
International Search Report, for International Application No. PCT/US2019/018620, date of mailing Apr. 22, 2019, pp. 1-3.
Written Opinion, for International Application No. PCT/US2019/018620, date of mailing Apr. 22, 2019, pp. 1-7.
Tian, B., et al., "Roadmap on Semiconductor-Cell Biointerfaces", Phys. Biol., Mar. 9, 2018, vol. 15, 031002, pp. 1-33.

Shuai Xu and John A. Rogers, "Transient Electronics and the Future of Medicine", Phys. Biol., Mar. 9, 2018, vol. 15, 031002, pp. 3-5.
Stefano Cestellos-Blanco and Peidong Yang, "Semiconductor-Microorganism Catalytic Biohybrid Systems for Artificial Photosynthesis", Phys. Biol., Mar. 9, 2018, vol. 15, 031002, pp. 6-8.
João L. Carvalho-de-Souza and Francisco Bezanilla, "Optocapacitance: Photostimulation without Cell Modification", Phys. Biol., Mar. 9, 2018, vol. 15, 031002, pp. 9-10.
Jia Liu and Zhenan Bao, "Roadmap of Polymer Bioelectronics-Cell Interface", Phys. Biol., Mar. 9, 2018, vol. 15, 031002, pp. 11-12.
Martin Hjort, Yuhong Cao and Nicholas Melosh, "Engineering Cell Access", Phys. Biol., Mar. 9, 2018, vol. 15, 031002, pp. 13-14.
Guglielmo Lanzani and Fabio Benfenati, "Organic Opto-Biointerfaces", Phys. Biol., Mar. 9, 2018, vol. 15, 031002, pp. 15-16.
Giulia Galli and Francois Gygi, "Predicting Interfacial Properties from First Principles Simulations: Semiconductors in Aqueous Media", Phys. Biol., Mar. 9, 2018, vol. 15, 031002, pp. 17-18.
Rylan Kautz and Alon A. Gorodetsky, "Revisiting a Classic Inspiration Source: Cephalopod-Derived Materials for Bioelectronics", Phys. Biol., Mar. 9, 2018, vol. 15, 031002, pp. 19-20.
Samuel S. Kim and Timothy K. Lu, "Accelerating Synthetic Biology with Approaches and Technologies from Semiconductor Engineering", Phys. Biol., Mar. 9, 2018, vol. 15, 031002, pp. 21-22.
Polina Anikeeva, "Addressing Signaling Complexity of the Nervous System", Phys. Biol., Mar. 9, 2018, vol. 15, 031002, pp. 23-24.
Michal Cifra, Ondrej Krivosudsky and Daniel Havelka, "High-Frequency Nanoscale Semiconductor Devices for Electric Sensing and Control of Proteins", Phys. Biol., Mar. 9, 2018, vol. 15, 031002, pp. 25-26.
Yuanwen Jiang and Bozhi Tian, "Silicon-Based Intracellular Biointerfaces", Phys. Biol., Mar. 9, 2018, vol. 15, 031002, pp. 27-32.
Jung, S.W., et al., "Neuron Stimulation Device Integrated with Silicon Nanowire-Based Photodetection Circuit on a Flexible Substrate", Sensors, 2016, vol. 16, Issue 2035, pp. 1-15.
Kwak, M., et al., "Interfacing Inorganic Nanowire Arrays and Living Cells for Cellular Function Analysis", Small, Sep. 9, 2015, vol. 11(42), pp. 5600-5610.
Parameswaran, R., et al., "Flexible Semiconductor-Polymer Hybrid Constructs for Optical Pacing of Cardiomyocyte", Materials Research Society Poster Presentation, Dec. 1, 2015.
Parameswaran, R., et al., "Silicon Nanowire Scaffold for Optical Pacing of Cardiomyocytes", Materials Research Society Poster Presentation, Nov. 28, 2016.
Koehler, K., et al., "Silicon Nanowire Based Scaffold for Optical Pacing of Cardiomyocytes", Materials Research Society Poster Presentation, Nov. 29, 2017.
Lee, C.H., et al., "Fabricating Nanowire Devices on Diverse Substrates by Simple Transfer-Printing Methods", PNAS, Jun. 1, 2010, vol. 107(22), pp. 9950-9955.
Wu, L., et al., "Automatic Release of Silicon Nanowire Arrays with a High Integrity for Flexible Electronic Devices", Scientific Reports, Feb. 3, 2014, vol. 4, Issue 3940, pp. 1-7.
Katherine Bourzac, Nanowires that Behave Like Cells, Aug. 11, 2019, MIT Technology Review.
Extended European Search Report from the European Patent Office, dated Nov. 2, 2021, for European Patent Application No. 19759936.8, pp. 1-8.
Parameswaran, R. et al. "Flexible Semiconductor-Polymer Hybrid Constructs for Optical Pacing of Cardiomyocytes," Materials Research Society Poster Abstract (Dec. 1, 2015).
Koehler, K., et al. "Silicon Nanowire Based Scaffold for Optical Pacing of Cariomyocytes," Materials Research Society Poster Abstract (Nov. 29, 2017).
U.S. Application No. 18/712,154, filed May 21, 2024.
U.S. Appl. No. 18/612,387, filed Mar. 21, 2024.
Tian, B. et al., "Coaxial silicon nanowires as solar cells and nanoelectronic power sources," Nature, vol. 449(18), pp. 885-890 (2007).

* cited by examiner

A

B

Figure 3, cont.
C
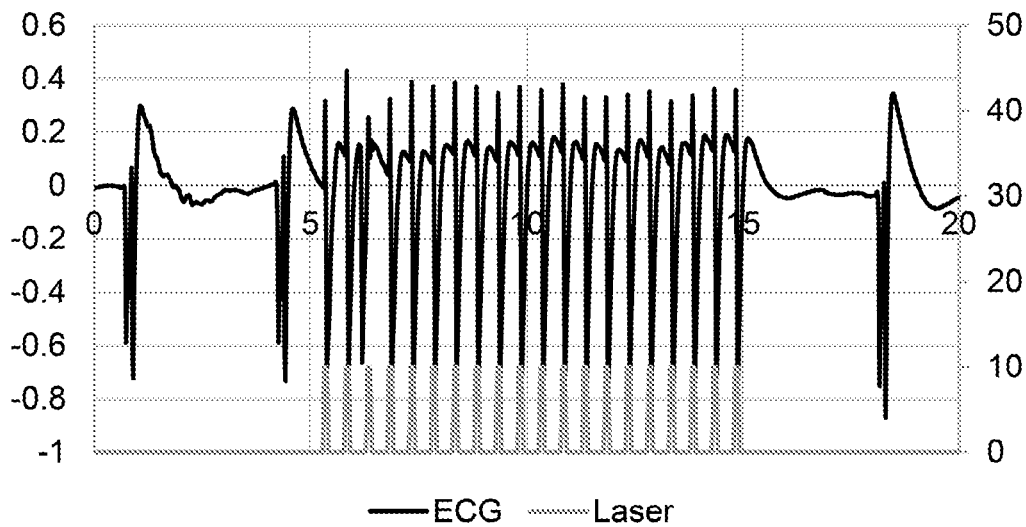
D
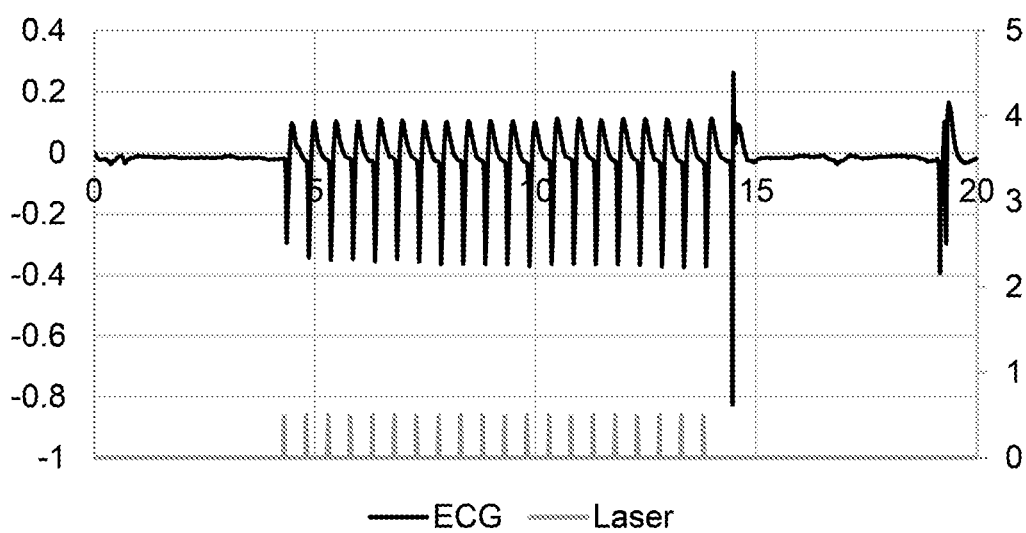

Figure 3, cont.
E
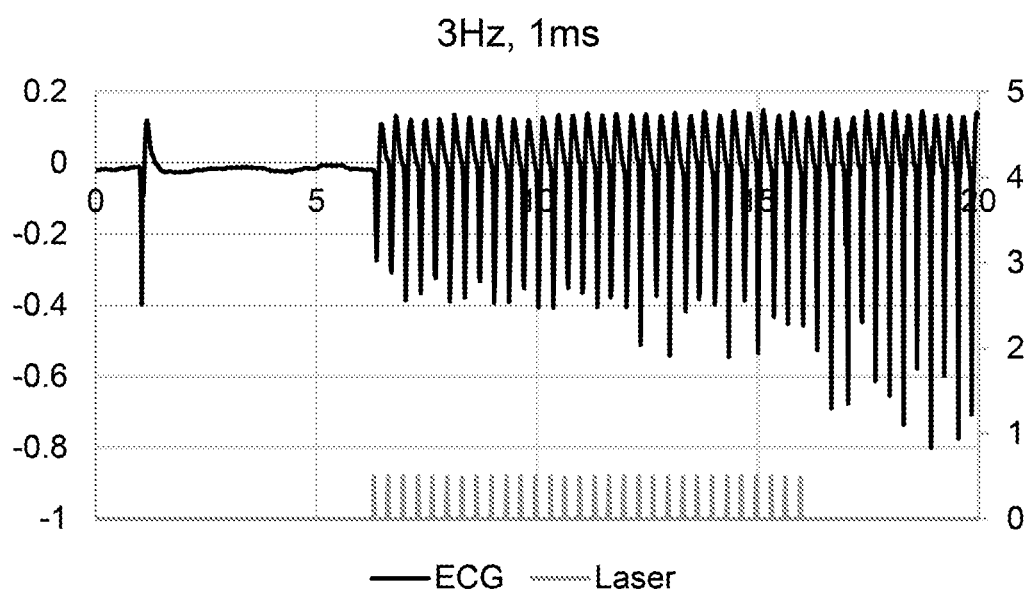

METHODS AND SYSTEMS FOR MODULATING CELLULAR ACTIVATION

CROSS-REFERENCE

This application is a 371 U.S. national phase of PCT/US2020/056106, filed Oct. 16, 2020, which claims priority from U.S. Provisional application No. 62/915,928, filed Oct. 16, 2019, both which are incorporated by reference in its entirety.

STATEMENT REGARDING FEDERALLY SPONSORED RESEARCH OR DEVELOPMENT

This invention was made with government support under grant number NS101488 awarded by the National Institutes of Health. The government has certain rights in the invention.

BACKGROUND OF THE DISCLOSURE

Field of the Disclosure

This disclosure relates to methods for modulating activity of cells and tissue with materials that are capable of being activated by light, such methods useful for treating diseases. The disclosure also provides devices and systems suitable for use in such methods, particularly devices and systems having oxygen ($O_2$) plasma-treated p-type (boron) silicon.

Technical Background

Extracellular electrical stimulation of excitable cells is the basis for many implantable devices that treat a variety of diseases. While these devices have been efficacious, they are often limited by their bulkiness, mechanical invasiveness, and inability to target single cells. Thus, researchers have looked to optical stimulation techniques, where organic or inorganic photodiode substrates are used for photovoltaic stimulation of cells, including neurons; however, these tools cannot be easily administered in a drug-like fashion. While some photothermally-modulating materials meet these criteria, chronic cellular effects due to heat from such devices are unknown. Optogenetics has been promising for addressing these issues, but fundamentally requires genetic modifications, which can be difficult to implement in vivo. As a result, there is still a need for exploring a non-genetic approach that can be administered in a drug-like fashion.

Silicon (Si) micro- and nano-materials are promising to address these concerns as they have been widely used for many biophysical or biomedical applications due to their highly tunable electrical and chemical properties, ability to absorb a broad range of wavelengths of light, and biocompatibility. Silicon materials, however, have not been widely used largely due to the limited understanding of the physicochemical processes at the material surfaces under physiological conditions.

Therefore, there exists a need for optical methods for modulating cellular behavior using silicon that are not mechanically invasive and do not require genetic manipulation of target cells, yet provide sub-cellular specificity.

SUMMARY OF THE DISCLOSURE

The inventors have found that $O_2$ plasma-treated Si-based devices can establish biointerfaces with cells (such as cardiomyocytes) or tissue (such as myocardium). The inventors have also found that the optical cellular-modulation can mimic naturally occurring extracellular signals, i.e., random, fast and multisite input signals, and that such modulation can modulate the activity of a cell or tissue.

Thus, one aspect of the disclosure provides silicon devices. Such devices, in certain embodiments, are $O_2$ plasma-treated p-type (boron type) silicon devices. In certain embodiments, the device of the disclosure is a membrane that includes a flexible substrate on which the device of the disclosure or a plurality of the devices of the disclosure are distributed Another aspect of the disclosure methods for modulating activity of a cell capable of being activated by light. Such methods include contacting a membrane of the cell with a device of the disclosure as described herein to form a structure-cell membrane interface; and exposing the interface to light under conditions to depolarize the cell membrane thereby increase a threshold for activation of the cell.

Another aspect of the disclosure provides methods of treating a disease in a subject by modulating activation of a cell. Such methods include (i) providing one or more devices of the disclosure as described herein (including membranes); and (ii) exposing the subject to light under conditions sufficient to increase a threshold for activation of the cell and treat the disease.

In certain embodiments, the methods of the disclosure treat a neuronal disease.

In certain other embodiments, the methods of the disclosure treat a cardiovascular disease. For example, in certain aspects of the disclosure, methods of the disclosure optically train myocardium to beat at a target frequency.

Thus, one aspect of the disclosure provides a method for optically training myocardium to beat at a target frequency. This method includes (i) contacting the myocardium with one or more devices of the disclosure as described herein (including membranes); and (ii) operating a light emitter to provide, during a training period of time, a plurality of pulses of light at a stimulation wavelength to the myocardium, wherein the plurality of pulses of light are provided at the target frequency.

The disclosure also provides systems suitable for use in the methods of the disclosure. Thus, in one aspect, the disclosure provides a system for treating a disease in a subject by modulating activation of a cell. Such system includes: (i) one or more devices of the disclosure as described herein or one or more membranes of the disclosure as described herein; (ii) a light emitter configured to emit light at a stimulation wavelength; and (iii) a controller that is operably coupled to the light emitter.

In certain embodiments of this aspect, the disclosure provides a system for optically training myocardium to beat at a target frequency. As provided herein, such system includes: (i) one or more devices of the disclosure as described herein or one or more membranes of the disclosure as described herein; (ii) a light emitter configured to emit light at a stimulation wavelength; and (iii) a controller that is operably coupled to the light emitter.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the invention will become apparent to those skilled in the art from this detailed description.

BRIEF DESCRIPTION OF THE DRAWINGS

The accompanying drawings are included to provide a further understanding of the systems and methods of the disclosure, and are incorporated in and constitute a part of this specification. The drawings are not necessarily to scale, and sizes of various elements may be distorted for clarity. The drawings illustrate one or more embodiment(s) of the disclosure and, together with the description, serve to explain the principles and operation of the disclosure.

FIG. 1B illustrates various surface morphologies obtained based on the duration of treatment with hydrofluoric acid, while

FIG. 2A shows the membrane placed under an upright microscope, and FIG. 2B provides photocurrents (black line) when the membrane is stimulated with a 530 nm LED (gray line).

DETAILED DESCRIPTION

Figure 1A:
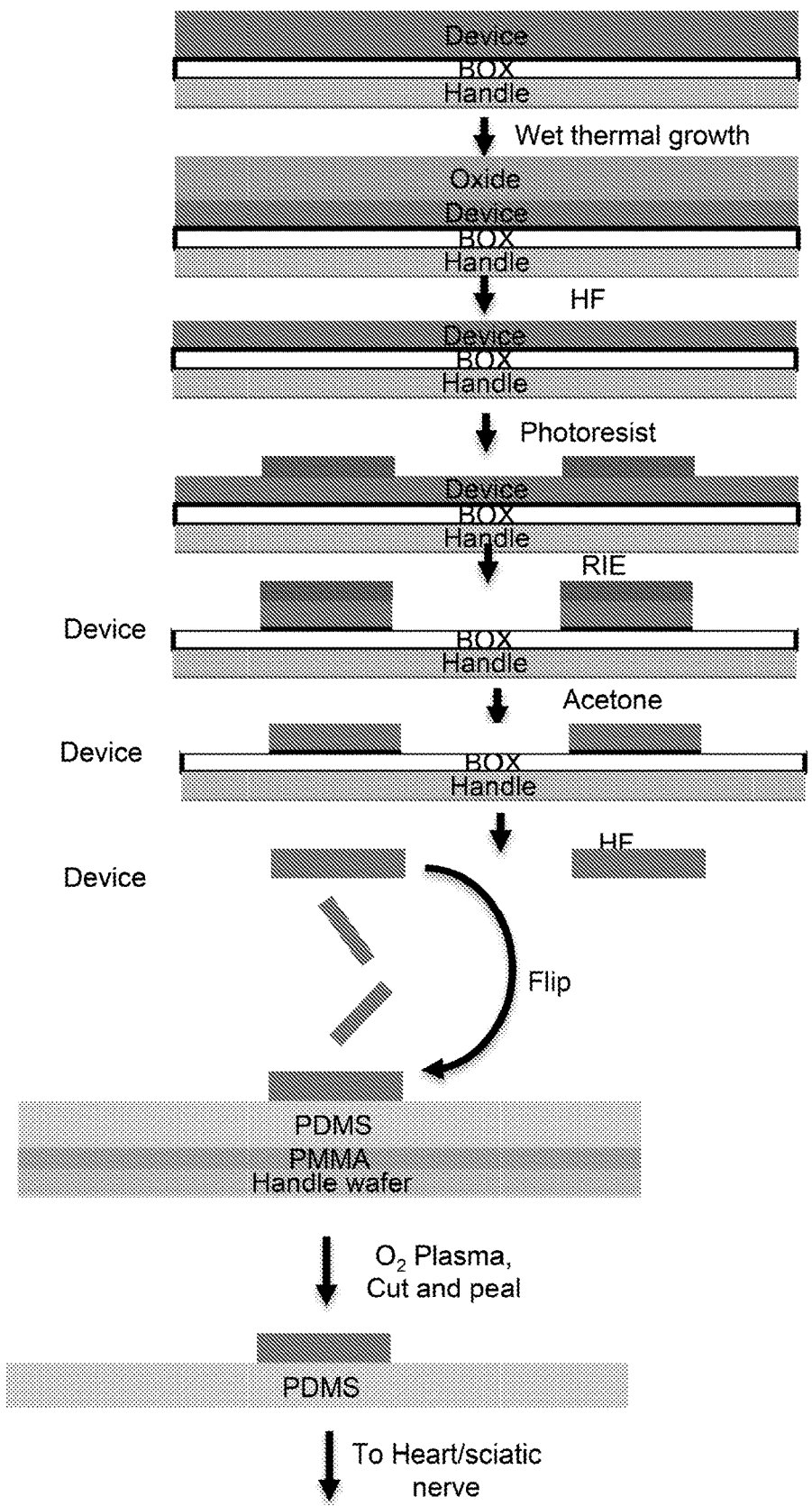
FIG. 1A illustrates the general method for preparing the device of disclosure.

Before the disclosed methods and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and systems described herein can be configured by the person of ordinary skill in the art to meet the desired need. As provided above, inventors have found that $O_2$ plasma-treated Si-based devices can establish biointerfaces with cells (e.g., cardiomyocytes) or tissue (e.g., myocardium). The inventors have also found that the optical cellular-modulation can mimic naturally occurring extracellular signals, i.e., random, fast and multisite input signals, and that such modulation can modulate the activity of a cell or tissue.

As provided above, one aspect of the disclosure methods for modulating activity of a cell capable of being activated by light. Such methods include contacting a membrane of the cell with a device of the disclosure as described herein to form a structure-cell membrane interface; and exposing the interface to light under conditions to depolarize the cell membrane thereby increase a threshold for activation of the cell.

In certain embodiments, the structure-cell interface is a direct interface between the device and the cell membrane (i.e., there are no intervening structures between the silicon device and the cell membrane). In certain embodiments of the methods of the disclosure, the silicon device contacts the membrane without penetrating the membrane. For example, the silicon device may rest on the surface of the cell membrane.

The methods of the disclosure modulate activity of a cell capable of being activated by light. Thus, in certain embodiments, any cell capable of being activated by light may be used in the methods of the disclosure. In some embodiments, the cell is a cardiomyocyte or a neuron. In certain embodiments, the cell is a cardiomyocyte. In certain embodiments, the cell is a neuron.

Another aspect of the disclosure provides methods of treating a disease in a subject by modulating activation of a cell. In certain embodiments of the disclosure, the method is treating a neuronal disease. In certain other embodiments, the methods of the disclosure treat a cardiovascular disease. For example, in certain aspects of the disclosure, methods of the disclosure optically train myocardium to beat at a target frequency. Thus, one aspect of the disclosure provides a method for optically training myocardium to beat at a target frequency. This method includes (i) contacting the myocardium with one or more devices of the disclosure as described herein (including membranes); and (ii) operating a light emitter to provide, during a training period of time, a plurality of pulses of light at a stimulation wavelength to the myocardium, wherein the plurality of pulses of light are provided at the target frequency. In certain embodiments, the device is a membrane that includes a flexible substrate on which the device of the disclosure or a plurality of the devices of the disclosure are distributed and the membrane is configured to be placed in contact with cells of the myocardium such that the devices are in contact with cells of the myocardium. The silicon devices provide, to cells of the myocardium that they are in contact with, excitatory stimulus in response to receiving light at the stimulation wavelength.

The method of the disclosure may be useful as cardiac resynchronization therapy (CRT). In such method, the myocardium is contacted with two or more devices of the disclosure as described herein.

The disclosure also provides systems suitable for use in the methods of the disclosure. As provided above, the disclosure provides a system for treating a disease in a subject by modulating activation of a cell. Such system includes (i) one or more devices of the disclosure as described herein or one or more membranes of the disclosure as described herein; (ii) a light emitter configured to emit light at a stimulation wavelength; and (iii) a controller that is operably coupled to the light emitter. In such systems, the devices provide, to the cell they are in contact with, excitatory stimulus in response to receiving light at the stimulation wavelength. The controller includes one or more processors, wherein the controller is programmed to perform controller operations including: operating the light emitter to provide the light to the cell.

In certain embodiments, the disclosure provides a system for optically training myocardium to beat at a target frequency. As provided herein, such system includes: (i) one or more devices of the disclosure as described herein or one or more membranes of the disclosure as described herein; (ii) a light emitter configured to emit light at a stimulation wavelength; and (iii) a controller that is operably coupled to the light emitter. In certain embodiments, the system is a membrane comprising that includes a flexible substrate on which a device or a plurality of devices of the disclosure as described herein are distributed and the membrane is configured to be placed in contact with a surface of the myocardium such that the devices are in contact with cells of the myocardium. The devices provide, to cells of the myocardium that they are in contact with, excitatory stimulus in response to receiving light at the stimulation wavelength. The controller includes one or more processors and is programmed to perform controller operations including: operating the light emitter to provide, during a training period of time, a plurality of pulses of light to the myocardium, wherein the plurality of pulses of light are provided at the target frequency.

It can be beneficial in a variety of applications to apply the devices (or membranes) as described herein to the stimulation and control of the activity of myocardium (e.g., myocardium of a heart of a person or animal). These devices can be used to efficiently control the pacing of a heart and/or to correct some other deleterious electrical and/or pacing condition of the heart (e.g., bradycardia, tachycardia, ventrical or atrial fibrillation). These devices may additionally or alternatively be used to "retrain" the electrical behavior of the myocardium of the heart, e.g., to train the heart tissue to beat at a more appropriate target rate, to change a pattern of electrical connection or conduction of the heart, or to train the myocardium of the heart in some other manner. The use of the devices of the disclosure may provide a variety of benefits relative to the use of electrodes to pace or otherwise manipulate the heart, e.g., by providing a more energy-efficient interface that has a mechanical compliance that is better matched to the heart tissue.

In order to use the devices described herein to facilitate optical control or manipulation of the electrical and/or physiological properties of myocardium, the silicon devices of the disclosure can be distributed on or within a substrate (e.g., a substrate formed from a polymer). In certain embodiments the substrate is a flexible substrate. Such devices on a substrate are also referred herein as membranes of the disclosure. In certain embodiments, the substrate is a polydimethylsiloxane (PDMS) substrate or poly(methyl methacrylate) (PMMA) substrate. The flexible substrate material can provide a base for the devices, facilitating their organization and implantation within a body (e.g., by contacting with a surface of a heart or some other surface of a myocardial tissue) such that, when the devices receive light at an appropriate wavelength, nearby cardiac cells receive electrical or other stimulus. The substrate, in certain embodiments, can also be a hard, inflexible substrate. One of skill in the art would be able to select suitable inflexible materials that can provide a base for the device.

The silicon devices can be used to provide pulses of optical stimulation in order to cause, manipulate, alter, or otherwise affect the electrical activity of cells of the myocardium. Such pulses of stimulation can provide an entraining stimulus, causing the myocardium to beat or otherwise become electrically active in time with the pulses of stimulation. However, reducing the total energy required to elicit the excitation in the cells of the myocardium for a specific location, pulse width, pulse amplitude, pulse waveform, or other parameters of stimulation is challenging. Yet a reduction of the total energy may be desirable in order to reduce the power requirements of a stimulator device, to reduce phototoxicity in the myocardium, to reduce an amount of localized heating of the myocardium, or to provide some other benefits.

In practice, it can be beneficial to quickly scan the illumination in a point, line, or other shape across the tissue to be stimulated. For example, a spot of illumination can be scanned across the tissue in a plurality of lines or according to some other scan pattern such that the entirety of the tissue surface is briefly illuminated respective periods of time across the scan period. This method was found to provide excellent stimulation of myocardium, especially for "training" the myocardium to pulse at a specified rate, while reducing the overall amount of illumination (e.g., the overall amount of illumination power) required to effect the stimulation. This may be due to the device(s) acting to waveguide and spread the illumination across the surface of the myocardium. Accordingly, each cell of the myocardium may receive a plurality of pulses of illumination during a particular scan, as the point (or line, or other shape) of illumination passes over and/or near the cell.

In certain embodiments, a point, line, or other shape of illumination can be scanned across an area of myocardium by operating a galvanometer to scan the output of a laser or other light-emitting element(s). Such a setup could be implemented in an implanted device setting, e.g., by providing a cowling over the devices, by using mirrors, lenses, optical fiber(s), or other elements to direct the output of the galvanometer to the flexible devices substrate, or in some other manner. Additionally or alternatively, such scanning of illumination across the surface of the myocardium could be accomplished by activating individual light-emitting elements (e.g., LEDs, VCSELs) of an array of light-emitting elements according to a scan pattern. Such light-emitting elements could be disposed on or otherwise directly associated with the flexible devices substrate (e.g., by disposed on the substrate or membrane on which the devices are distributed, by being disposed on a flexible PCB or other substrate that is, in turn, adhered to the membrane substrate). Alternatively, the light-emitting elements could be coupled to respective different locations across the area of the flexible devices substrate, e.g., via respective optical fibers.

In order to stimulate the myocardium to pulse at a target frequency and/or to train the myocardium to pulse at such a target frequency independent of continued stimulation, pulses of illumination may be applied to the myocardium as described above. Each pulse of stimulation could include one or more scans of the illumination across the tissue. For example, a single pulse of illumination could include two or more scans of a point of illumination across the tissue, with the scans repeated at a specified frequency (e.g., 1 kHz). Multiple pulses may be provide during a training period, e.g., at a frequency corresponding to the target myocardial beat frequency (e.g., between 0.5 and 3 Hz). In order to train the myocardium to continue pulsing at the trained frequency, multiple periods of training pulses may be provided, each period of training pulses being separated from the others by a "break period" during which illumination is not provided. The duration of such a break period may be optimized, e.g., to have a two minute duration.

Note that the above methods used the fluorescent and/or electrical detection of cardiomyocyte pulse rate to assess the efficacy of the methods described herein to entrain the electrical activity of myocardium and/or of cardiac cells in culture. However, such detection may also be employed in an implant or other system used to effect training of myocardium in a clinical setting. Such a detected pulse rate may be used to determine whether training pulses should be applied to the myocardium, e.g., by determining that the detected pulse rate has deviated from a target frequency by more than a threshold amount. Additionally or alternatively, the detected pulse rate could be used to determine whether sufficient training has been provided, and if not, to provide additional training pulses. For example, a first set of training pulses could be provided and the pulse rate following the training pulses could be detected. If the detected pulse rate deviated from a target by more than a threshold amount, additional training pulses could be provided.

The methods of the disclosure require exposing the interface to light under conditions to depolarize the cell membrane. The depolarization of the cell membrane thereby increases a threshold for activation of the cell. The amount of light needs to be sufficient to accomplish polarization, yet low enough to not harm the cell. Thus, suitable exposing time, wavelength, and power of the light will be selected so to provide the desired activity without the toxicity to the cell. The exposing time may be for a time ranging from 0.5 ms to 15 ms. For example, in certain embodiments, the interface may be exposed for 0.5 ms to 10 ms, or 0.5 ms to 7 ms, or 0.5 ms to 5 ms, or 0.5 ms to 2 ms, or 0.5 ms to 1 ms, or 1 ms to 15 ms, or 1 ms to 10 ms, or 1 ms to 7 ms, or 1 ms to 5 ms, or 1 ms to 2 ms, or 2 ms to 15 ms, or 2 ms to 10 ms, or 2 ms to 7 ms, or 2 ms to 5 ms, or 5 ms to 15 ms, or 5 ms to 10 ms, or 5 ms to 7 ms, or 10 ms to 15 ms. In certain embodiments, the cell is a neuron cell and the exposure time is or 0.5 ms to 7 ms, or 0.5 ms to 5 ms, or 1 ms to 7 ms, or 1 ms to 5 ms. In certain embodiments, the cell is a cardiomyocyte and the exposure time is or 1 ms to 200 ms, or 1 ms to 100 ms, or 10 ms to 100 ms, or 50 ms to 100 ms, or 10 ms to 50 ms.

In certain embodiments, a single pulse is sufficient to modulate activity of a cell. In certain embodiments, two or more pulses are sufficient to modulate activity of a cell. In certain embodiments, 5 or more, or 10 or more, or 25 or more, or 50 or more pulses are sufficient to modulate activity of a cell. In certain embodiments, 1 to 5, or 1 to 10, or 1 to 25, or 1 to 50, or 1 to 100, or 2 to 5, or 2 to 10, or 2 to 25, or 2 to 50, or 2 to 100, or 5 to 10, or 5 to 25, or 5 to 50, or 5 to 100 pulses are sufficient to modulate activity of a cell.

The selection of the wavelength may be determined on the type of silicon device and the amount of light energy required to deactivate the cell without toxicity to the cell. The light may be provided at an excitation wavelength ranging from 400 to 900 nm. For example, in certain embodiments, the light may be provided at an excitation wavelength ranging from 400 to 800 nm, or 400 to 750 nm, or 400 to 600 nm, or 400 to 550 nm, or 500 to 900 nm, or 500 to 800 nm, or 500 to 750 nm, or 500 to 600 nm, or 600 to 900 nm, or 600 to 800 nm, or 600 to 750 nm. The light may be provided at a power in a range of 1 mW to 1 W. For example, in certain embodiments, the light may be provided at a power in a range of 10 mW to 1 W, or 100 mW to 1 W, or 500 mW to 1 W, or 1 mW to 500 mW, or 10 mW to 500 mW, or 100 mW to 500 mW.

As noted above, the methods and systems of the disclosure generally require silicon devices. The devices of the disclosure include any microscale or nanoscale object that can be used in any of the embodiments described herein unless otherwise specified. Devices include nanowires, nanotubes, nanoscaffolds such as mesh and membrane, nanorods, nanowhiskers, and other suitable geometries. "Nanowire" (also "NW," "SiNW," or "silicon NW") as used herein is a nanoscopic wire that is generally a solid wire, and may be elongated in some cases. "Nanotube" is generally nanoscopic wire that is hollow, or that has a hollowed-out core. "Nanoscaffold" is generally a free-standing porous scaffolds such as mesh and membrane. The silicon mesh can be made by photolithography and have a random or regular network of 3D features that can, for example, mimic the size scale and morphology of submicron bioactive extracellular matrices (ECMs). The devices, in some embodiments, may be formed having dimensions of at least about 1 μm, at least about 3 μm, at least about 5 μm, at least about 10 μm, at least about 20 μm, at least about 50 μm, or at least about 100 μm in length, and can be less than about 100 μm, less than about 50 μm, less than about 20 μm, less than about 10 μm, less than about 5 μm, less than about 3 μm, less than about 2 μm, less than about 1 μm, less than about 100 nm, less than about 80 nm, less than about 60 nm, less than about 40 nm, less than about 20 nm, less than about 10 nm, or less than about 5 nm in diameter or thickness (height and width). The devices, in some embodiments, may be formed having dimensions of in a range of about 1 μm to about 5 μm, or range of about 2 μm to about 5 μm, range of about 1 μm to about 3 μm in diameter or thickness (height and width). The devices may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

In some embodiments, at least a portion of a device is doped. As used herein, a "doped" device is a device for which a dopant is incorporated substantially throughout the crystalline lattice of the device, as opposed to a device in which a dopant is only incorporated in particular regions of the crystal lattice at the atomic scale, for example, only on the surface or exterior. "Heavily doped" and "lightly doped" are terms the meanings of which are clearly understood by those of ordinary skill in the art. In some cases, one or more regions may comprise a single monolayer of atoms ("delta-doping"). In certain cases, the region may be less than a single monolayer thick (for example, if some of the atoms within the monolayer are absent). As a specific example, the regions may be arranged in a layered structure within the device, and one or more of the regions may be delta-doped or partially delta-doped.

In certain embodiments, the device contains p-doped regions or is p-doped.

In certain embodiments, the device is undoped.

In certain embodiments, the device is oxygen plasma-treated silicon. In certain embodiments, the device is oxygen plasma-treated p-doped silicon. In certain embodiments, the device is created using wet thermal oxide growth. In certain embodiments, in addition to oxygen-plasma, one or more other gases may be introduced during the plasma treatment. Other gases include, but are not limited to, argon (Ar), chlorine ($Cl_2$), nitrogen ($N_2$), sulfur hexafluoride ($SF_6$), silicon tetrachloride ($SiCl_4$), carbon tetrafluoride ($CF_4$), fluoroform ($CHF_3$), difluoromethane ($CH_2F_2$), hexafluoroethane ($C_2F_6$), and octafluoropropane ($C_3F_8$).

The devices of the disclosure may be plasma treatment for a time ranging from 10 seconds to 60 minutes. For example, in certain embodiments, the plasma treatment is for a time ranging from 1 min to 60 min, e.g., 1 min to 30 min, or 1 min to 20 min, or 1 min to 20 min; or for a time ranging from 5 min to 60 min, e.g., 5 min to 45 min, or 5 min to 30 min, or 5 min to 20 min, or 5 min to 15 min, or 5 min to 10 min; or for a time ranging from 10 min to 60 min, e.g., 10 min to 45 min, or 10 min to 30 min, or 10 min to 20 min.

The devices of the disclosure may be treated with acid, such as hydrofluoric acid (conc. 10-49%) prior to plasma treatment. The acid treatment, in certain embodiments, may be for a time ranging from 1 hours to 72 hours. For example, in certain embodiments, the acid treatment is for a time ranging from 12 hours to 72 hours, e.g., 12 hours to 48 hours, or 12 hours to 24 hours, or 1 hour to 24 hours, 1 hour to 12 hours.

In certain other embodiments, the devices are free or substantially free of gold, silver, or platinum.

The silicon device may be freestanding. As used herein, "freestanding" device means a device free of contact with another device (but not excluding contact of a type that may be desired between individual devices, e.g., as in a crossbar array). For example, a "freestanding" structure may, at some point in its life, not be attached to another structure, for example, with another device, or the free-standing article maybe on a polymer or in solution. This is in contrast to nanotubes produced primarily by laser vaporization techniques that produce materials formed as ropes having diameters of about 2 nm to about 50 nm or more and containing many individual nanotubes (see, for example, Thess, et al., "Crystalline Ropes of Metallic Carbon Nanotubes," *Science*, 273:483-486 (1996)). This is also in contrast to conductive portions of structure which differ from surrounding material only by having been altered chemically or physically, in situ, i.e., where a portion of a uniform article is made different from its surroundings by selective doping, etching, etc. A "freestanding" structure is one that can be (but need not be) removed from the location where it is made, as an individual structure, and transported to a different location and combined with different components to make a functional device such as those described herein and those that would be contemplated by those of ordinary skill in the art upon reading this disclosure.

In certain embodiments, the silicon device may be freestanding and suspended in a pharmaceutically acceptable solution, paste, or a hydrogel. The silicon device may be partially suspended or resting on the surface of the pharmaceutically acceptable solution, paste, or a hydrogel. For example, in certain embodiments, one surface of the silicon device is in contact (e.g., covered) with the pharmaceutically acceptable solution, paste, or a hydrogel, while the other surface of the silicon device is uncovered.

The silicon device may be distributed in a flexible substrate comprising one or more of polymers. Distributed silicon device may be partially embedded or on the surface (e.g., bound to the surface) of the flexible substrate. In certain embodiments, partially embedded includes 10%, or 20%, or 30%, or 40%, or 50%, or 60%, or 70%, or even 80% of the total weight of silicon device is embedded into the flexible substrate.

Many suitable flexible substrates are known in the art. In certain embodiments, the flexible substrate is a polymer. In some embodiments, the polymer is selected from a photoresist polymer, a biocompatible polymer, a biodegradable polymer, an extracellular matrix protein, and a combination thereof. In some embodiments, the flexible substrate comprises PDMS. In certain embodiments, the flexible substrate comprises PMMA. In certain embodiments, the flexible substrate comprises PDMS or PMMA, and SU-8 photoresist. In certain embodiments, the flexible substrate is a biodegradable polymer including, but not limited to, poly lactic-co-glycolic acid (PLGA), poly(ethylene glycol) diacrylate (PEGDA), collagen, and gelatin.

In certain embodiments, the flexible substrate has an open porosity of at least about 30%. For example, the flexible substrate has an open porosity of at least about 40%, or 45%, or 50%, or 55%, or even 60%.

Although the Si-based materials are composed primarily of silicon, they can include measurable amounts of other elements. In embodiments, the silicon devices include oxygen. The oxygen may form bonds with silicon such that the oxygen (and some of the silicon) is in the form of an oxide, $SiO_x$.

In certain other embodiments, the devices are free or substantially free of oxygen, and silicon oxide, $SiO_x$.

In an example embodiment, the device comprises a p-type silicon and PDMS as the flexible substrate. These devices may have a geometry, layer thickness, composition, or other configuration specified such that the device provides electrical stimulation when it receives light within a specified range of stimulation wavelengths, e.g., between 900 nanometers and 400 nanometers or between 740 nanometers and 530 nanometers.

The particulars shown herein are by way of example and for purposes of illustrative discussion of certain embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following embodiments and claims) are to be construed to cover both the singular and the plural, unless otherwise indicated herein or clearly contradicted by context.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

All percentages, ratios and proportions herein are by weight, unless otherwise specified.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the disclosure are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of various aspects of the disclosure are described herein, including the best mode known to the inventors for carrying out the methods described herein. Of course, variations on these described embodiments will become apparent to those of ordinary skill in the art upon reading the foregoing description. The skilled artisan will employ such variations as appropriate, and as such the methods of the disclosure can be practiced otherwise than specifically described herein. Accordingly, the scope of the disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

EXAMPLES

Certain aspects of the disclosure are illustrated further by the following examples, which are not to be construed as limiting the disclosure in scope or spirit to the specific methods and materials described in them.

Example 1: Synthesis of p-Type Silicon Device and Membrane

The general method for preparing the device of the disclosure is illustrated in FIG. 1A. In short, a silicon-on-insulator (SOI) wafer with device layer of p (boron) type Si with Resistivity of 0.001-0.01 Ω·cm, and 2-5 µm thickness was used. In certain cases, SOI was thinned to 3 µm using $SF_6$ reactive ion etching (RIE). Then, wet thermal oxide layer ($SiO_2$; 1 µm) was grown on the SOI wafer, and then removed with HF resulting in a device layer with thickness approximately ~2-3 µm. Standard photolithography was then used to create several different features and shapes. Photoresist was removed by sonication in acetone. The device was then released by 49% HF overnight. The devices were removed, flipped, and mounted on a polydimethylsiloxane (PDMS) substrate or poly(methyl methacrylate) (PMMA) substrate. The device was then treated by oxygen plasma (600 W) for about 10 minutes. The device was cut and gently remover from the wafer using isopropyl alcohol/acetone and a tweezer.

Figure 1B:
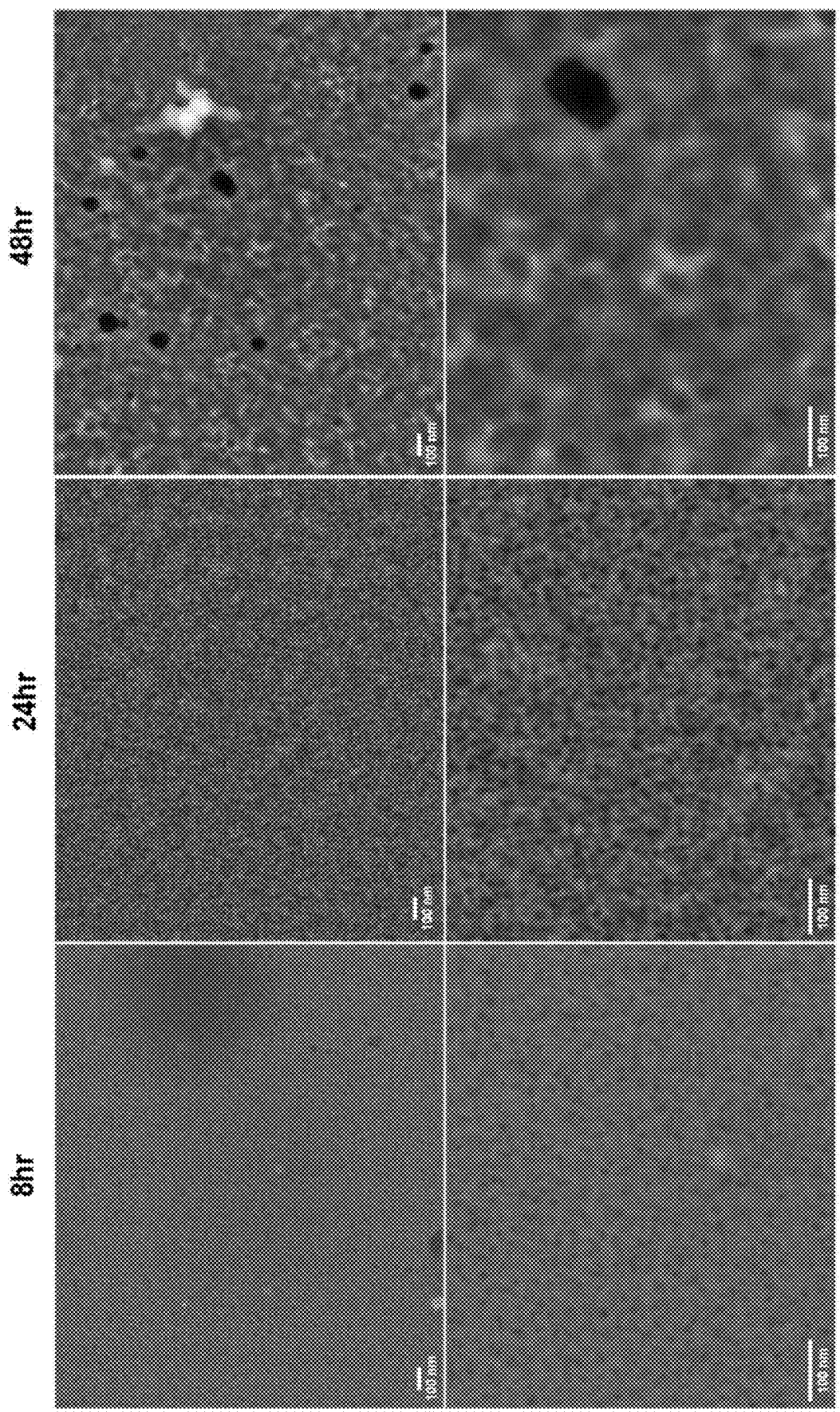

Due to the treatment of the device with hydrofluoric acid, pores are formed on the surface and increase the electrochemical surface area of the device. Different duration of treatment creates different surface morphologies on the device and are illustrated in FIG. 1B.

Figure 1C:
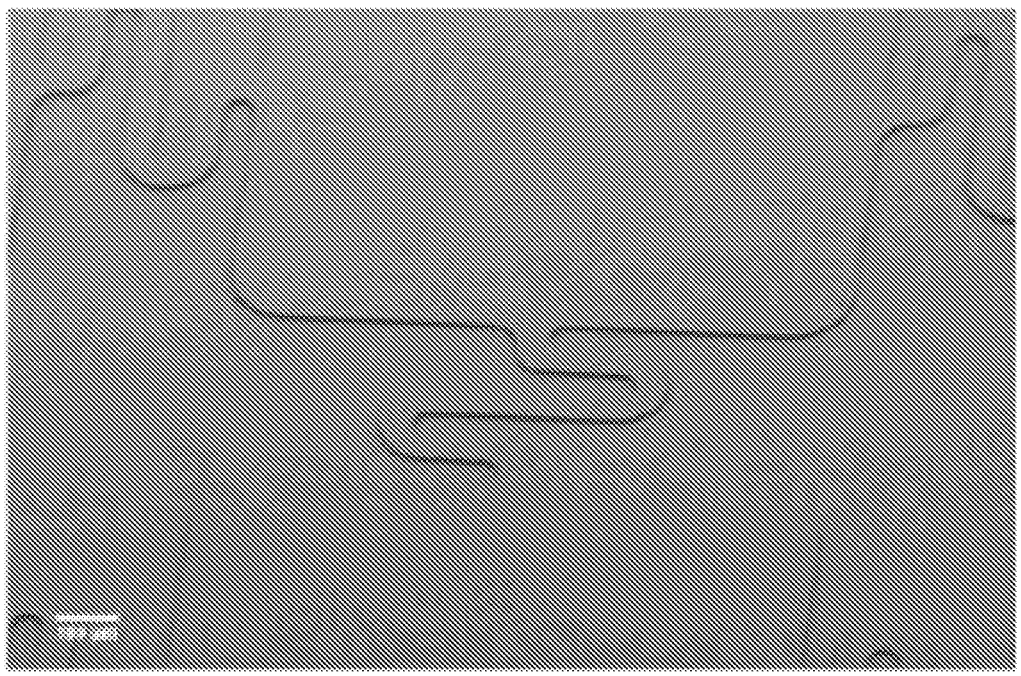
FIG. 1C illustrates various shapes and patterns obtained using the method for preparing the device of disclosure.
Figure 1C:
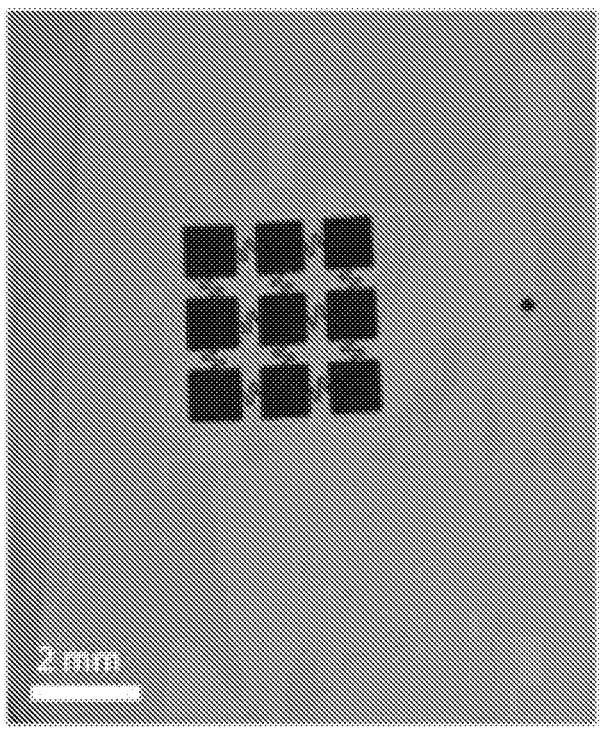
Figure 1C:
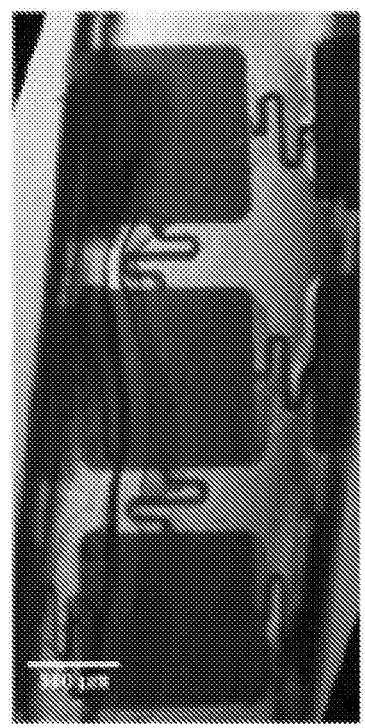

Different shapes or patterns created in the material can ensure its flexibility around the tissues. As illustrated in FIG. 1C, the membranes are pattern into 3 rows by 3 column arrays of squares where squares are connected with each other using a think flexible connecting trace, made of the same material.

Figure 1D:
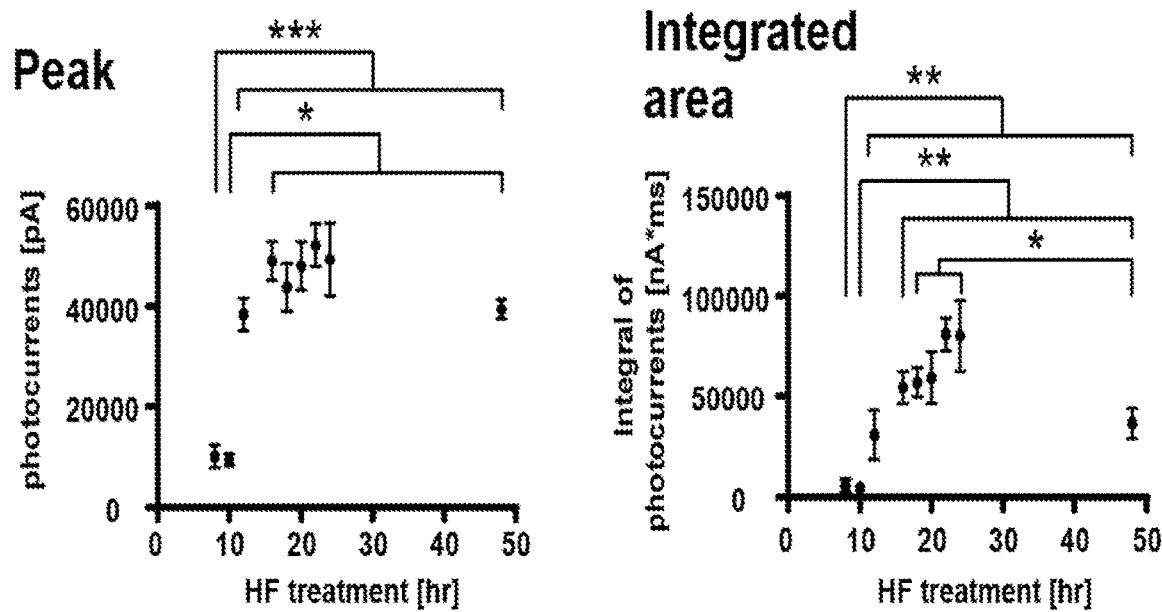
FIG. 1D shows the dependence of the photocurrent generated from the devices of the disclosure depending on the HF treatment duration.
Figure 1E:
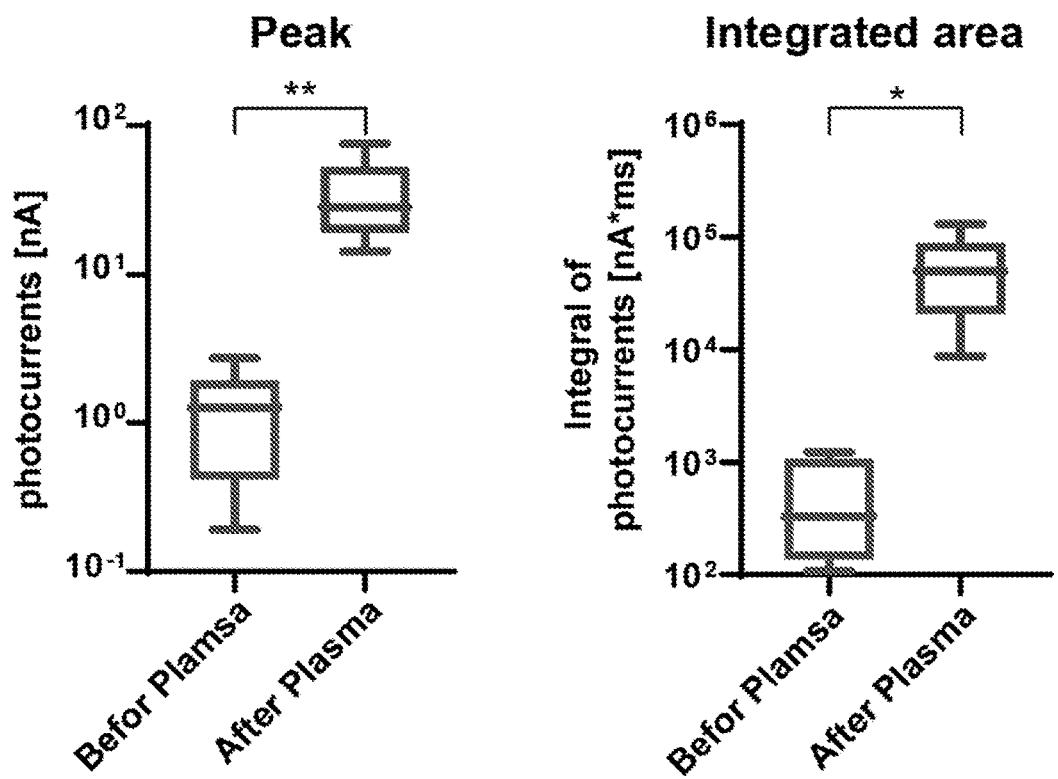
FIG. 1E shows the dependence of the photocurrent generated from the devices of the disclosure before and after $O_2$ plasma treatment.

The dependence of the photocurrent generated from the devices are illustrated on the FIG. 1D, which clearly indicates the importance of the optimal treatment time on the photocurrents generated. For the aforementioned material the optimal treatment duration was determined to be 20 to 24 hours but might be different for other types of silicon substrates, doping, thickness, device patterns and possible additional surface modifications. The dependence of the photocurrent generated from the devices before and after $O_2$ plasma treatment are illustrated in FIG. 1E, which clearly indicates increase 100-times fold increase of the photocurrents generated from the device after oxygen plasma treatment.

The device on a substrate (i.e., the membrane) of the disclosure prepared by this method can be readily placed on the heart/sciatic nerve.

Example 2: Measurements of the Photocurrents Generated by the Membrane

Figure 2A:
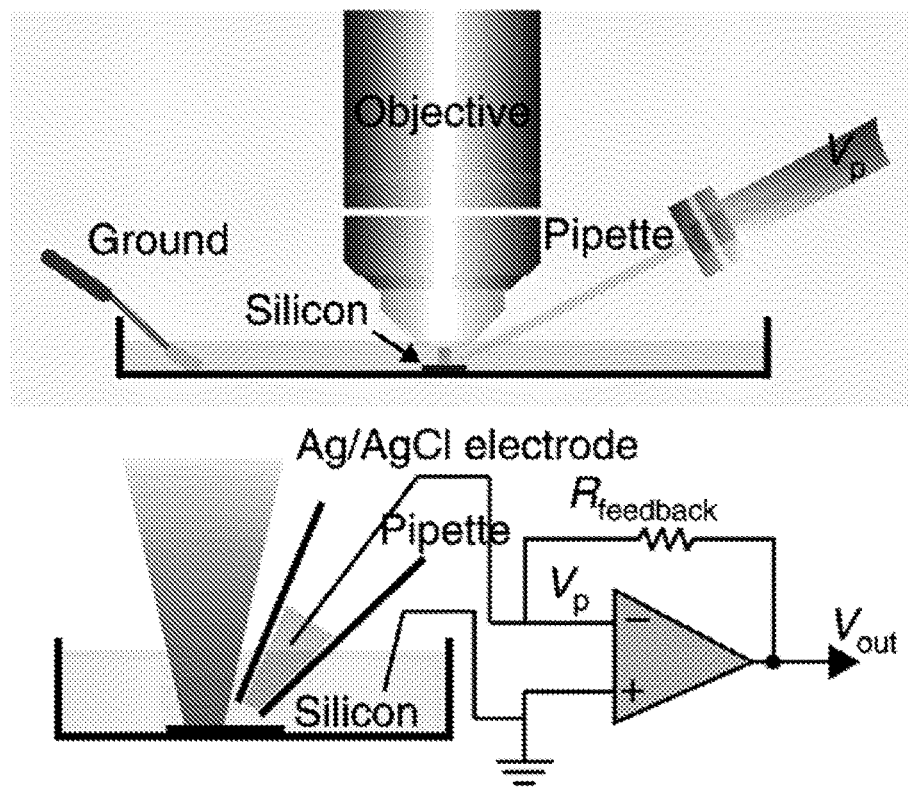
FIGS. 2A and 2B illustrate measuring photocurrents generated by the membrane.

The membranes were placed in phosphate buffered saline (PBS) under an upright microscope as illustrated in FIG. 2A. LED pulses (530 nm, about 17 mW, 500 µm diameter) were applied through a microscope. A patch electrode was placed right on top the membrane and recorded the resulting photocurrents. The stimulated membrane generated photocurrents that were measured by the patch system and recoded with a micropipette with 1 MΩ resistance.

Figure 2B:
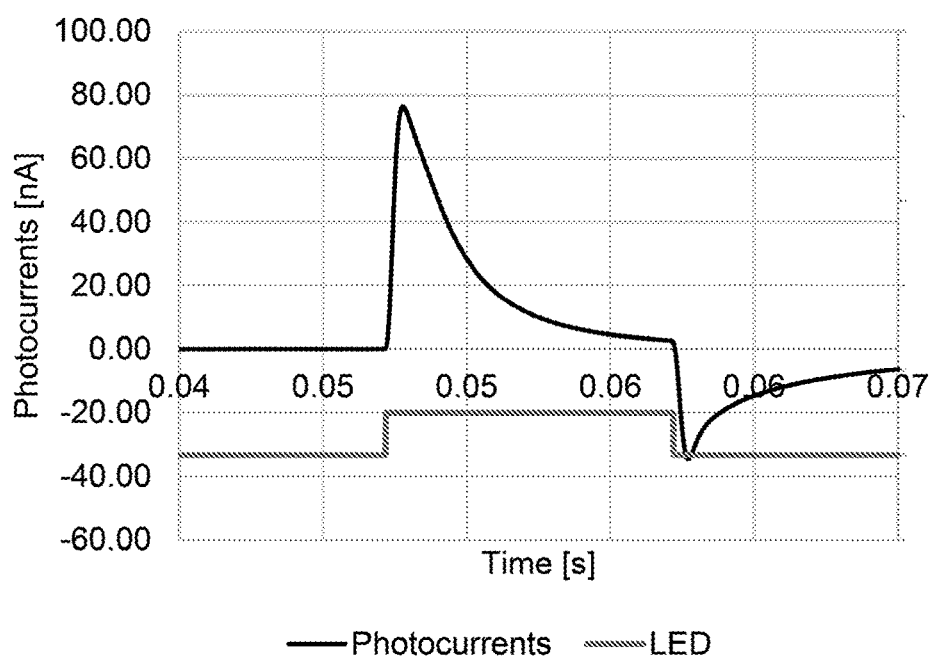

As provided in FIG. 2B, the membrane stimulated with a 530 nm LED (gray line) resulted in photocurrents shown as black line. The membrane of the disclosure generated photocurrents that are higher than those previously observed using p-i-n junction and gold decoration by Jiang et al. ("Rational design of silicon structures for optically controlled multiscale biointerfaces." *Nature biomedical engineering* 2.7 (2018): 508; incorporated by reference herein).

Example 3: Optical Pacing of an Isolated Heart

The membranes of the disclosure were mounted on an isolated heart (using Langendorff apparatus) and stimulated using a collimated 532 nm laser or 477 nm pulses with durations of 1 ms, 10 ms, or 100 ms. The electrocardiogram (ECG) was recorded by electrodes connected to the aorta and left ventricle. Alternatively, the membrane mounted on a PMMA sacrificial layer was treated with acetone to remove the PMMA and released, then moved to PBS and mounted on the heart with no supporting layer.

Figure 3:
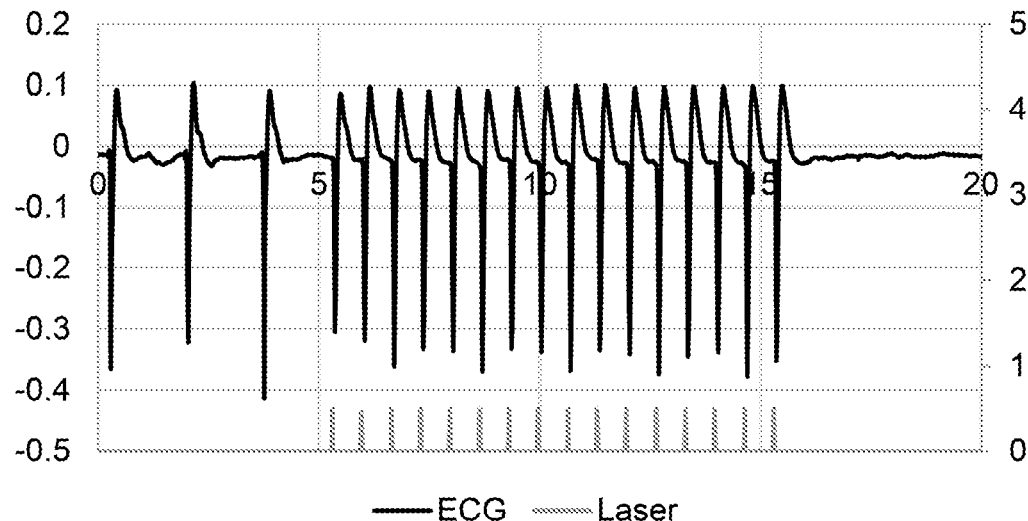
FIG. 3 illustrates the results of the optical training according to one embodiments of the methods of the disclosure. Panels A-E illustrate the results at different optical pacing rates: 1.5 Hz (A and B), 2 Hz (C and D), and 3 Hz (E).
Figure 3:
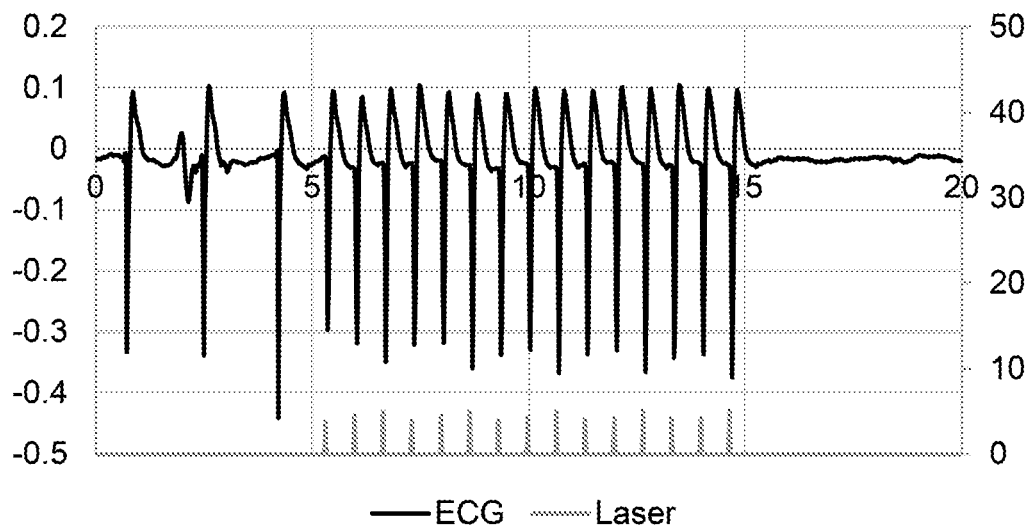

The results of the optical training are provided in FIG. 3. The ECG (black line) shows a slow spontaneous contracting rate (originated form the AV node). Upon optical stimulation, the heart is immediately paced and synchronized to the optical pacing rate of 1.5 Hz (panels A and B), 2 Hz (panels C and D), or 3 Hz (panel E).

Figure 4:
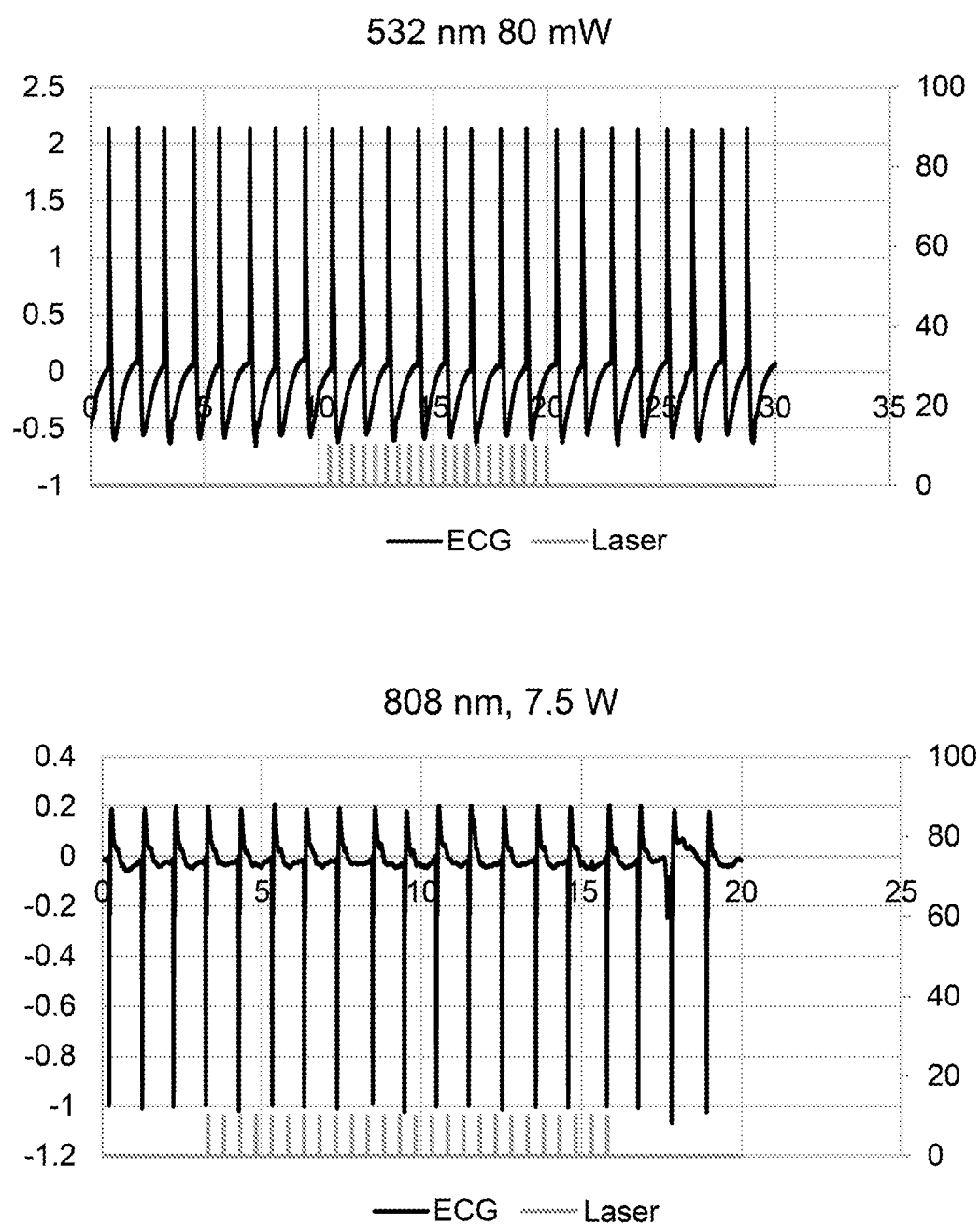
FIG. 4 illustrates the results of the optical training using the pin membranes with gold decoration not according to the methods of the present disclosure. Top graph was generated using a collimated 532 nm laser (80 mW) and the bottom graph was generated using an 808 nm laser with high power (7.5 W) pulses with durations of 1 and 200 ms.

In contrast to the membranes of the disclosure, the pin membranes with gold decoration did not pace the heart as provided in FIG. 4. Such membranes were mounted on an isolated heart and stimulated using a collimated 532 nm laser (80 mW) or an 808 nm laser with high power (7.5 W) pulses with durations of 1 and 200 ms. Despite much higher laser power, the ECG in FIG. 4 (black line) shows a slow spontaneous contracting rate with no effect on the rhythm upon optical stimulation.

Example 4: Pacing Threshold

Figure 5:
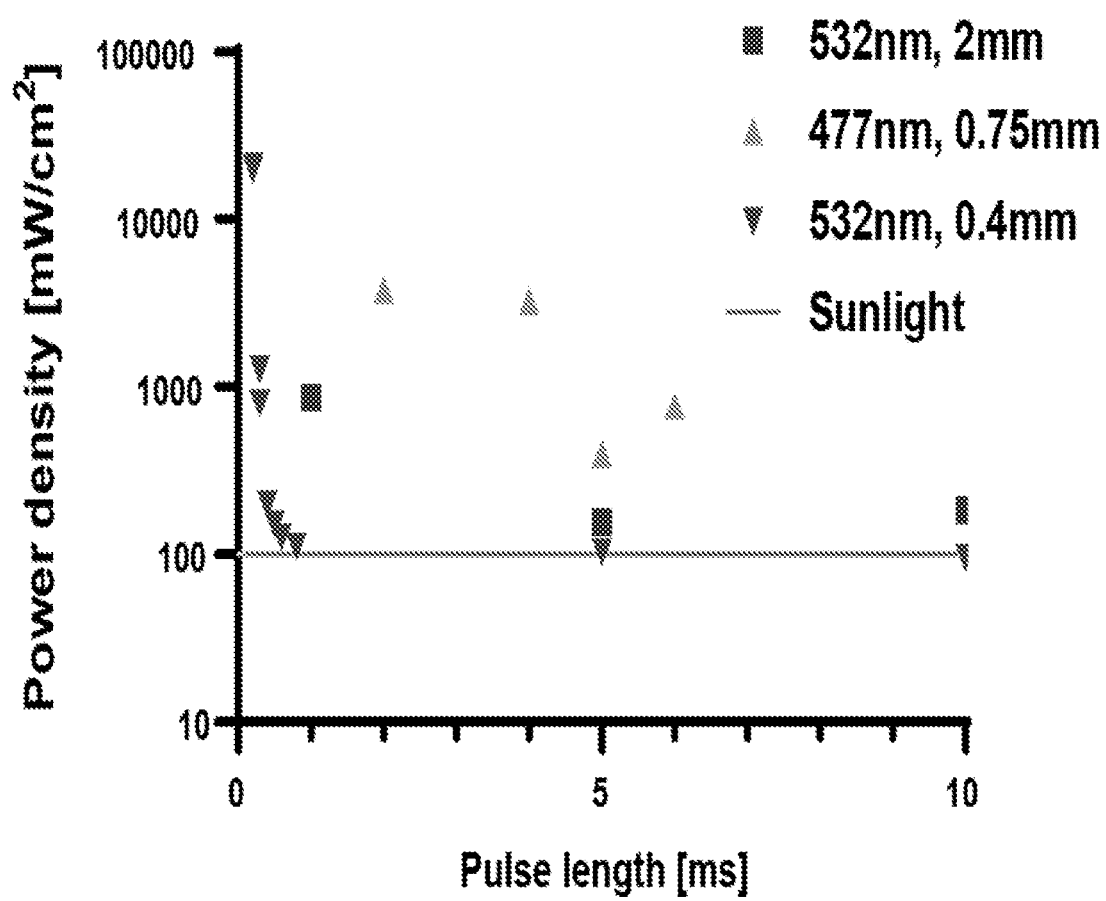
FIG. 5 shows the power density threshold for stimulation as a function of the pulse duration performed using 477 nm laser, 532 nm laser with two different beam sizes.

The power threshold for optical pacing was measured by gradually increasing the power. This was performed for the 532 laser with two different beam sizes (de-collimated), and with the 477 laser. The lowest power for which overdrive pacing was observed was determined as the pacing threshold. For each condition, the power threshold and the power density (calculated per the beam size) were found. This is illustrated in FIG. 5, which shows the laser power presented as the power density as a function of the pulse duration.

Example 5: Optical Pacing of the Sciatic Nerve

Figure 6A:
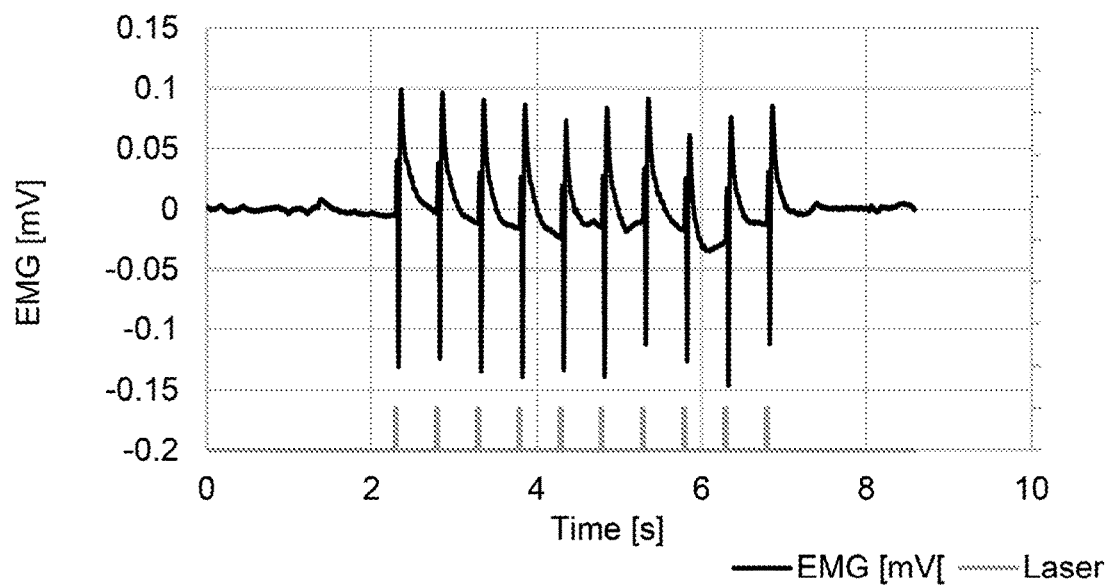
FIG. 6A illustrates the optical pacing of the sciatic nerve according to one embodiments of the methods of the disclosure.
Figure 6A:
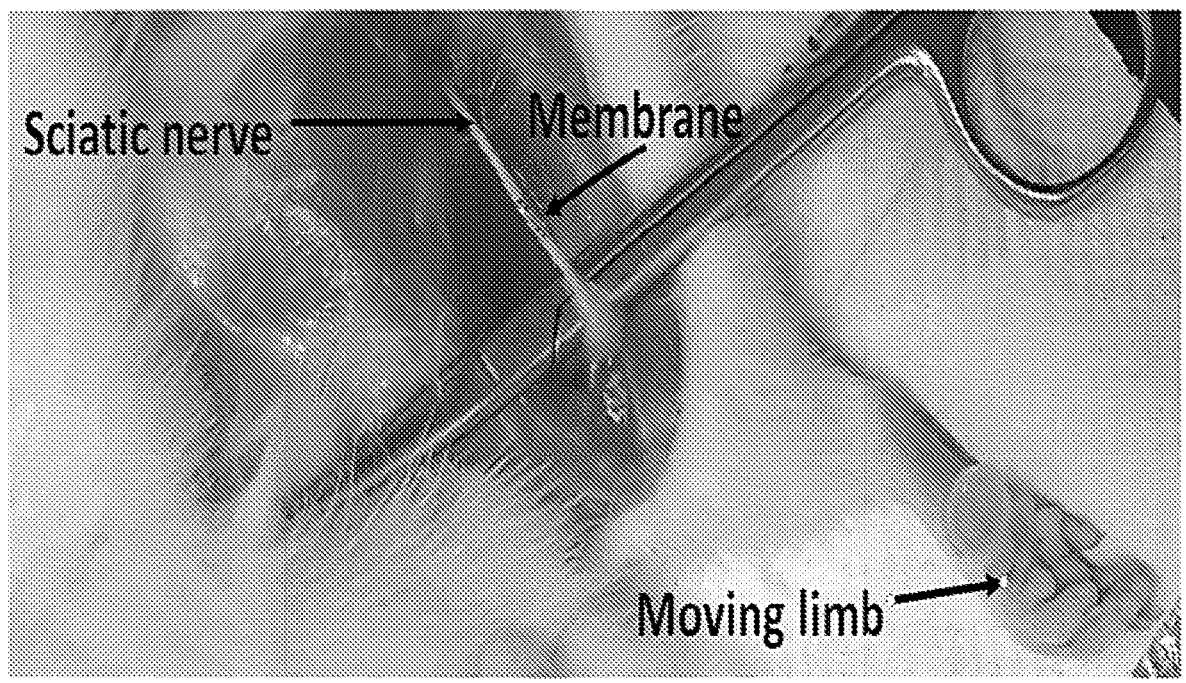

The sciatic nerve on an adult rat was exposed as shown in FIG. 6A (bottom panel). A free-standing membrane (from the PMMA substrate) was wrapped around it. Then, 532 nm collimated laser pulses were applied on the membrane. The pulses resulted in clear action potential (AP) that was recorded with the electromyography (EMG) (FIG. 6A, top panel, black top line). Each pulse also resulted in the rat's limb moving as a result of the AP propagating to the muscle (data not shown). Therefore, using the membrane of the disclosure and laser stimulation of the sciatic nerve provided a clear movement of the stimulate limb.

Figure 6B:
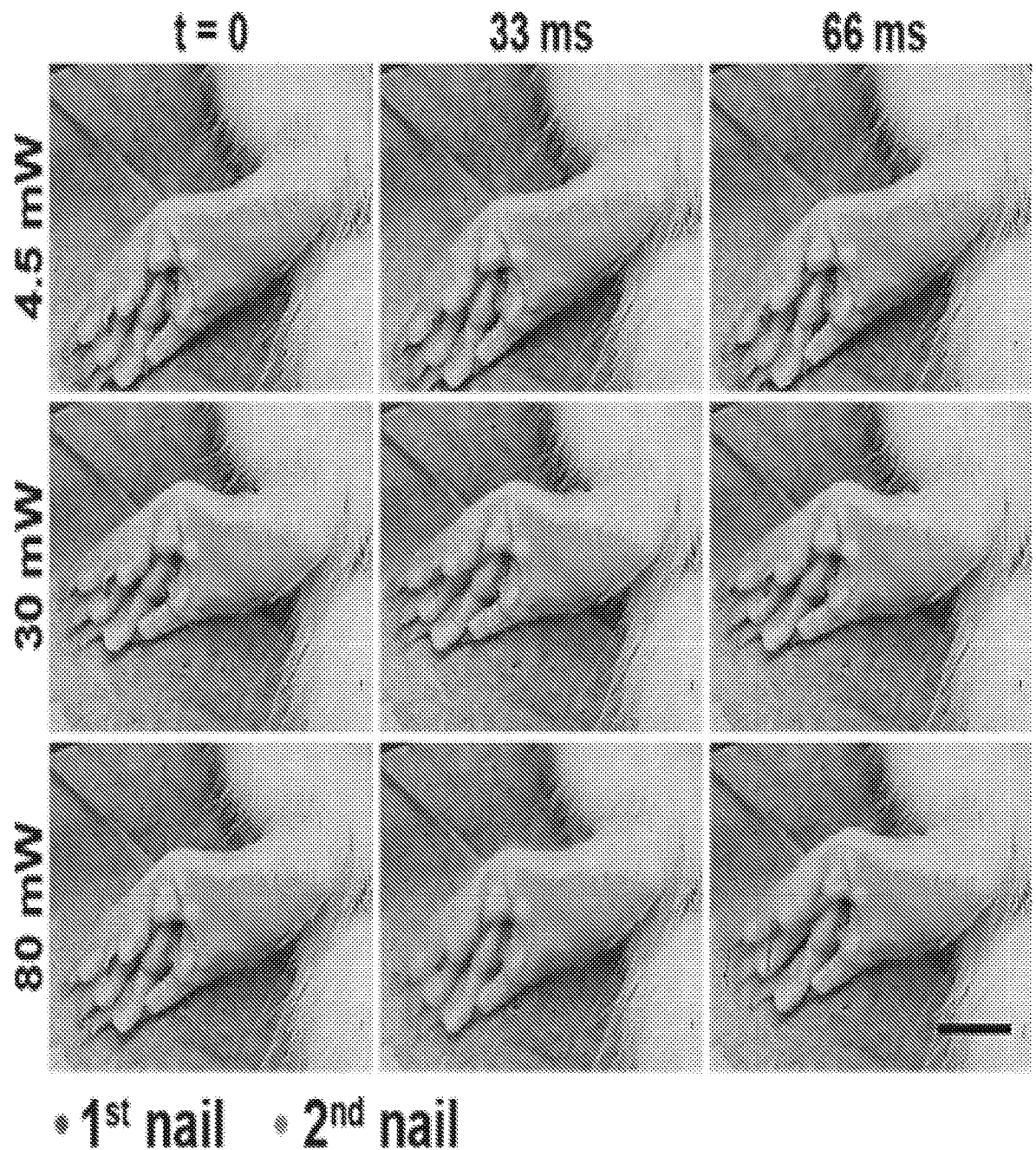
FIG. 6B illustrates the movement of the animal limb when different optical powers were delivered to the same membrane.
Figure 6C:
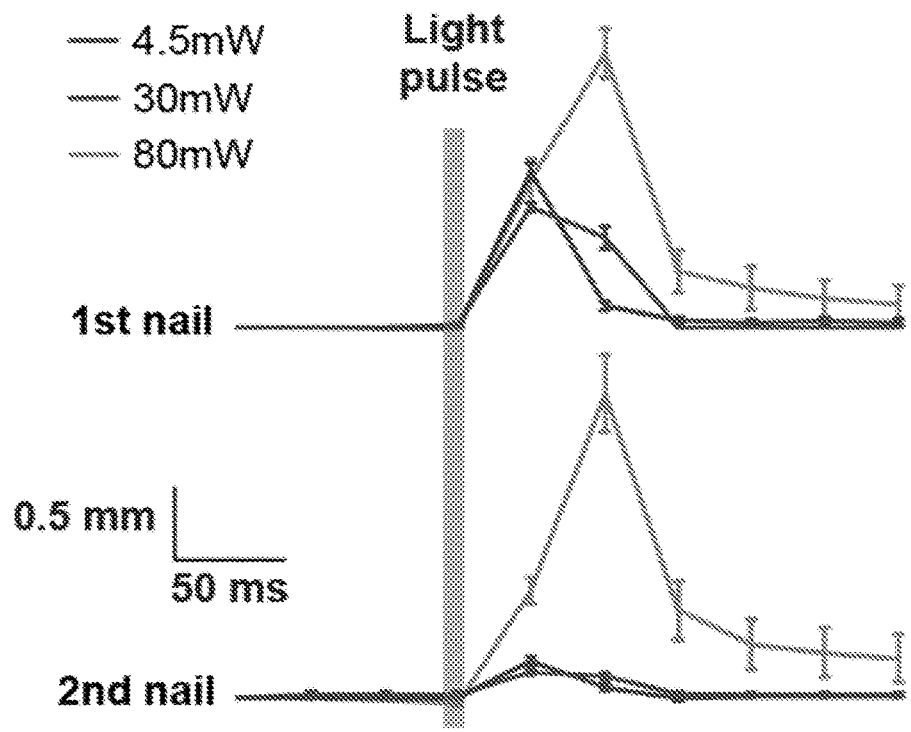
FIG. 6C shows the results of tracking two nails to follow their displacement due to the different optical stimulation density.
Figure 6C:
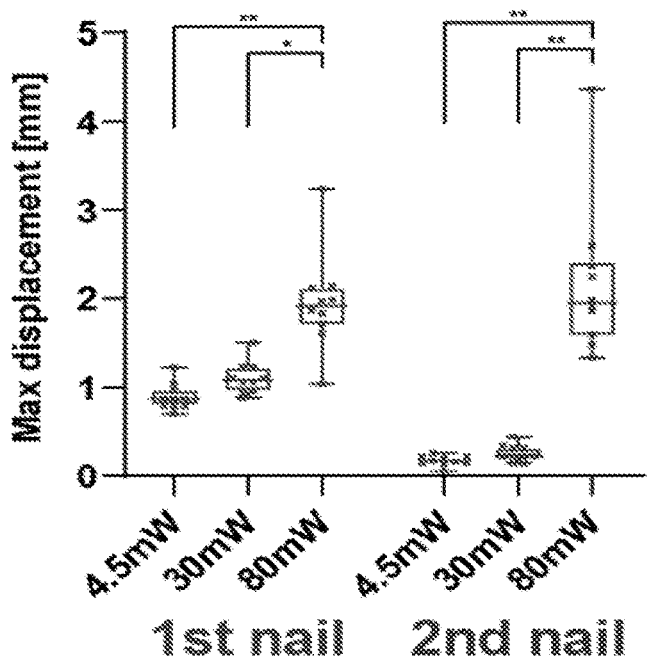

The sciatic nerve had shown an intensity dependent effect on the outcome of stimulation of an animal limb. FIG. 6B illustrates the movement of the animal limb, when different optical powers were delivered to the same membrane. Two nails were tracked to follow their displacement due to the different optical stimulation density, and the quantitative results of tracking are illustrated in FIG. 6C.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A method of treating a disease in a subject by modulating activation of a cell, the method comprising:
contacting a cell of the subject with an oxygen ($O_2$) plasma-treated p-type silicon device comprising a porous surface due to hydrofluoric acid treatment; and
exposing the device to light under conditions sufficient to increase a threshold for activation of the cell and treat the disease.

2. The method of claim 1, wherein the disease is a cardiovascular disease or a neuronal disease.

3. The method of claim 1, wherein the exposing is for a time ranging from 0.5 ms to 15 ms.

4. The method of claim 1, wherein the light is provided at an excitation wavelength ranging from 400 to 900 nm.

5. The method of claim 1, wherein the light is provided at a power in a range of 1 mW to 1 W.

6. The method of claim 1, wherein the device is treated with oxygen plasma for a time ranging from 10 seconds to 60 minutes.

7. The method of claim 1, wherein the device is distributed on a flexible substrate comprising one or more of polymers selected from a photoresist polymer, a biocompatible polymer, a biodegradable polymer, an extracellular matrix protein, and a combination thereof.

8. The method of claim 7, wherein the flexible substrate has an open porosity of at least about 30%.

9. The method of claim 1, wherein the device is distributed on a polydimethylsiloxane flexible substrate.

10. The method of claim 7, wherein the flexible substrate is configured to be placed in contact with the cell such that the device is in contact with the cell.

11. The method of claim 1, wherein the porous surface has an increased electrochemical surface area compared to a surface of a device without hydrofluoric acid treatment.

12. The method of claim 1, wherein the hydrofluoric acid treatment is for a time ranging from 1 to 72 hours.

* * * * *